United States Patent
Daley et al.

(10) Patent No.: US 6,613,028 B1
(45) Date of Patent: Sep. 2, 2003

(54) TRANSFER DELAY FOR INCREASED ACCESS FLUFF CAPACITY

(75) Inventors: Michael Allen Daley, Alpharetta, GA (US); Tamara Lee Mace, Doraville, GA (US); David Michael Matela, Alpharetta, GA (US); Yvette Lynn Hammonds, Fond du Lac, WI (US); Eugenio Go Varona, Marietta, GA (US); Arthur Edward Garavaglia, Alpharetta, GA (US); Laura Jane Walker, Appleton, WI (US); Ann Marie Giencke, Menasha, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/218,851

(22) Filed: Dec. 22, 1998

(51) Int. Cl.$^7$ ................................................ A61F 13/15
(52) U.S. Cl. .................. 604/385.01; 604/358
(58) Field of Search ................. 604/358, 380, 604/367, 385.01

(56) References Cited

U.S. PATENT DOCUMENTS

| | | |
|---|---|---|
| 3,338,992 A | 8/1967 | Kinney |
| 3,341,394 A | 9/1967 | Kinney |
| 3,344,789 A | 10/1967 | Arnold et al. |
| 3,502,763 A | 3/1970 | Hartmann |
| 3,542,615 A | 11/1970 | Dobo et al. |
| 3,692,618 A | 9/1972 | Dorschner et al. |
| 3,802,817 A | 4/1974 | Matsuki et al. |
| 3,849,241 A | 11/1974 | Butin et al. |
| 3,886,941 A | 6/1975 | Duane et al. |
| 3,934,588 A | 1/1976 | Mesek et al. |
| 3,967,623 A * | 7/1976 | Butterworth et al. ......... 602/45 |
| 4,015,604 A | 4/1977 | Csillag |
| 4,223,677 A * | 9/1980 | Anderson .................... 604/365 |
| 4,340,563 A | 7/1982 | Appel et al. |
| 4,585,449 A | 4/1986 | Karami |
| 4,657,538 A * | 4/1987 | Becker et al. ............... 604/378 |
| 4,758,240 A | 7/1988 | Glassman |
| 4,762,521 A | 8/1988 | Roessler et al. |
| 4,795,668 A | 1/1989 | Krueger et al. |

(List continued on next page.)

FOREIGN PATENT DOCUMENTS

| | | |
|---|---|---|
| DE | 25 13 251 A1 | 9/1976 |
| DE | 196 09 462 | 9/1997 |
| EP | 0 432 882 A2 | 6/1991 |
| FR | 2 044 554 | 2/1971 |
| WO | WO 90/14813 | 12/1990 |

OTHER PUBLICATIONS

A.A. Burgeni and C. Kapur: *Capillary Sorption Equilibria in Fiber Masses*, Textile Research Journal, 356–366, May 1967.

Josias VD Westhuizen and J. Prieur Du Plessis: *Quantification of Unidirectional Fiber Bed Permeability*, Journal of Composite Materials, 619–637, vol. 28, No. 7, 1994.

Primary Examiner—Weilun Lo
Assistant Examiner—Linh Truong
(74) Attorney, Agent, or Firm—Pauley Petersen Kinne & Erickson

(57) ABSTRACT

A personal care absorbent article having a fluid intake/distribution layer, a fluid transfer delay layer disposed beneath said fluid intake/distribution layer, said fluid transfer delay layer enabling the transfer of fluid from the fluid intake/distribution layer(s) to a pad layer disposed beneath the fluid transfer delay layer while still allowing fluid distribution by the fluid intake/distribution layer along the machine direction of the article resulting in saturation levels of less than or equal to about 0.86 g/g/in of fluid in the intake/distribution layer(s) and/or essentially equal to or greater than 0.06 g/g/in. of fluid in the pad layer.

21 Claims, 1 Drawing Sheet

U.S. PATENT DOCUMENTS

| | | | |
|---|---|---|---|
| 4,908,026 A | * | 3/1990 | Sukiennik et al. .......... 604/378 |
| 4,988,344 A | | 1/1991 | Reising et al. |
| 4,988,345 A | | 1/1991 | Reising |
| 4,994,037 A | * | 2/1991 | Bernardin ................... 604/368 |
| 5,037,409 A | * | 8/1991 | Chen et al. ................. 604/358 |
| 5,057,368 A | | 10/1991 | Largman et al. |
| 5,069,676 A | | 12/1991 | Ito et al. |
| 5,069,970 A | | 12/1991 | Largman et al. |
| 5,104,396 A | | 4/1992 | Oatley et al. |
| 5,108,820 A | | 4/1992 | Kaneko et al. |
| 5,108,827 A | | 4/1992 | Gessner |
| 5,277,976 A | | 1/1994 | Hogle et al. |
| 5,294,482 A | | 3/1994 | Gessner |
| 5,300,053 A | | 4/1994 | Genaro |
| 5,336,552 A | | 8/1994 | Strack et al. |
| 5,378,528 A | * | 1/1995 | Makoui ..................... 428/219 |
| 5,382,400 A | | 1/1995 | Pike et al. |
| 5,423,786 A | | 6/1995 | Fung et al. |
| 5,431,643 A | | 7/1995 | Ouellette et al. |
| 5,439,458 A | | 8/1995 | Noel et al. |
| 5,454,801 A | | 10/1995 | Lauritzen |
| 5,458,963 A | * | 10/1995 | Meirowitz et al. .......... 428/221 |
| 5,460,623 A | | 10/1995 | Emenaker et al. |
| 5,462,537 A | | 10/1995 | Carr et al. |
| 5,466,410 A | | 11/1995 | Hills |
| 5,514,120 A | | 5/1996 | Johnston et al. |
| 5,533,991 A | | 7/1996 | Kirby et al. |
| 5,536,555 A | | 7/1996 | Zelazoski et al. |
| 5,540,992 A | | 7/1996 | Marcher et al. |
| 5,562,650 A | | 10/1996 | Everett et al. |
| 5,569,226 A | * | 10/1996 | Cohen et al. ............... 428/137 |
| 5,643,240 A | * | 7/1997 | Jackson et al. ............. 604/378 |
| 5,647,862 A | * | 7/1997 | Osborn et al. ............. 604/368 |
| 5,658,639 A | | 8/1997 | Curro et al. |
| 5,665,082 A | * | 9/1997 | Boulanger .................. 428/103 |
| 5,669,895 A | * | 9/1997 | Murakami et al. .......... 604/358 |
| 5,679,042 A | | 10/1997 | Varona |
| 5,700,254 A | * | 12/1997 | McDowall et al. ......... 604/358 |
| 5,803,920 A | * | 9/1998 | Gilman ...................... 604/378 |
| 5,879,343 A | * | 3/1999 | Dodge et al. ............... 428/212 |
| 5,916,969 A | * | 6/1999 | Wang et al. ................ 524/378 |
| 5,919,177 A | * | 7/1999 | Georger et al. ............. 156/163 |
| 5,931,823 A | * | 8/1999 | Stokes et al. ............... 604/358 |
| 5,986,167 A | * | 11/1999 | Arteman et al. ............. 604/380 |
| 5,994,615 A | * | 11/1999 | Dodge et al. ............... 442/212 |
| 6,011,195 A | * | 1/2000 | Muhs et al. ................. 604/367 |
| 6,060,638 A | * | 5/2000 | Paul et al. ................... 604/367 |
| 6,168,849 B1 | * | 1/2001 | Braverman et al. ......... 428/137 |
| 6,203,654 B1 | * | 3/2001 | McFall et al. ............... 156/268 |
| 6,319,239 B1 | * | 11/2001 | Daniels et al. ......... 604/385.01 |

* cited by examiner

TRANSFER DELAY FOR INCREASED ACCESS FLUFF CAPACITY

BACKGROUND OF THE INVENTION

1. Field of the Invention

This invention relates to absorbent articles, particularly absorbent structures which are useful in personal care products such as disposable sanitary napkins, diapers, incontinence garments, and the like. More particularly, this invention relates to absorbent systems that must manage complex viscous body fluids such as menses.

2. Description of Prior Art

Absorbent articles such as feminine pads or sanitary napkins, diapers and incontinence garments are intended to intake and retain body fluids. Desired performance objectives of these articles include low leakage from the product and a dry feel to the wearer. Currently available products suffer from higher than desired leakage levels, producing stains on clothing, and are not perceived by users to fully deliver on other consumer attributes such as dryness, fit, comfort and continence. Leakage can occur due to a variety of shortcomings in the product, not the least of which is an insufficient rate of fluid uptake by the absorbent system, particularly on the second or third liquid surges. This is particularly problematic with feminine care products intended for overnight use where high loadings are often incurred requiring significant fluid retention capacity in order to hold the majority of the fluid.

Most commercially available sanitary pads have relatively high leakage rates, failing as much as 30% of the time. Such failures are believed to be due to the highly viscous nature of menses and the great variability in delivery volume which results in overloading of the pad in the target area and subsequent leaking. Insufficient distribution of menses is believed to be one of the key causes of the target area overloading.

In the field of urine management in personal care products like diapers, distribution is often provided by materials that have small pores with a narrow pore size distribution. These materials must move the high volume, low viscosity urine insults out of the target area in a time sufficient for the target area to be able to accept the next insult. The movement of urine may be to relatively remote parts of the diaper, overcoming substantial hydrostatic pressure. In contrast thereto, feminine hygiene products experience lower total insult volumes, but the fluid is of greater viscosity, making it more difficult to move the fluid. Distribution materials must be quite different for feminine hygiene products than for products concerned primarily with urine management.

Absorbent articles have typically employed various types of absorbent pads composed of cellulosic fibers. Particular absorbent garments may configure to control the distribution of absorbed liquids. For example, an absorbent article can have a liquid permeable transport layer which is located between a top sheet layer and an absorbent body. In other configurations, a conventional absorbent member can have fluid storage and acquisition zones composed of cellulosic fluff mixed with absorbent gelling particles and may include a dual-layer absorbent core arrangement comprising a bottom fluff pad containing hydrogel particles, and a top fluff pad with little or no hydrogel particles.

Non-woven materials such as carded webs and spunbond webs have been used as the body side liners in absorbent products. Specifically, very open, porous liner structures have been employed to allow liquid to pass through them rapidly and help keep the body skin separated from the wetted absorbent pad beneath the liner. Some structures have incorporated zoned surfactant treatments in preselected areas of the liners to increase the wettability of the preselected regions and thereby control the amount of liquid wet-back onto a wearer's skin. In addition, other layers of material, such as those constructed with thick, lofty fabric structures, have been interposed between the liner and absorbent pad for the purpose of reducing wet-back.

With conventional fluff-based absorbent structures, such as those discussed above, the cellulosic fibers, when wetted, can lose resiliency and collapse. As a result, the liquid uptake rate of the wetted structures may become too low to adequately accommodate subsequent, successive liquid surges. Where absorbent gelling particles are incorporated between the fibers to hold them apart, the gelling particles swell and do not release the absorbed fluid. Swelling of the particles can then diminish the void volume of the absorbent structure and reduce the ability of the structure to rapidly uptake fluids.

The addition of more absorbent material, such as secondary fluff pledgets, or absorbent gelling particles, has been employed to increase holding capacity. The desired rate of liquid intake within such arrangements, however, may not be sufficiently sustained during successive liquid surges.

Despite the development of absorbent structures as discussed hereinabove, there remains a need for improved absorbent structures which can adequately reduce the incidence of leakage from absorbent products, such as feminine hygiene products. There is a need for an absorbent structure which can provide improved handling of liquid surges and more effectively uptake and retain repeated loadings of liquid during use.

SUMMARY OF THE INVENTION

Accordingly, it is one object of this invention to provide a feminine hygiene product having superior distribution and transfer performance to allow movement of menses from a target area and provide comfort, dry feeling, and lower leakage than traditional such products.

It is another object of this invention to provide an overnight use feminine hygiene product having the capacity to hold the majority of fluids resulting from the high loadings which have been observed in such overnight products.

The overnight feminine hygiene products typically are thick maxipads with a 600 gsm basis weight fluff pad and fluff insert, which fluff material is present in the product for aesthetic and pad shaping reasons. It is one object of this invention to provide an absorbent system which enables utilization of the potential fluid storage capacity in the fluff.

It is yet another object of this invention to provide a feminine hygiene product such as an Ultrathin, Maxi, Overnite, Curved, Securehold and the like which provides good distribution and fluid transfer thus promoting absorbency and dryness.

These and other objects of this invention are achieved by a personal care absorbent article comprising a fluid intake/distribution layer, a fluid transfer delay layer disposed beneath the fluid intake/distribution layer, which fluid transfer delay layer enables fluid transfer from the fluid intake/distribution layer resulting in a fluid saturation of less than or equal to about 0.86 g/g/in in the fluid intake/distribution layer, and a pad layer disposed beneath the fluid transfer delay layer having a fluid saturation level essentially equivalent to or greater than 0.06 g/g/inch. The fluid intake/ distribution layer is comprised of stabilized, highly wettable fibers arranged to provide capillary pore sizes and a degree of wettability ideally suited to wick visco-elastic fluids, which layer, when exposed to visco-elastic fluids and simulants, demonstrates improved fluid distribution performance in terms of the distance wicked, the wicking rate, as well as the amount of fluid moved. The fluid intake/distribution layer comprises a class of distribution materials composed of stabilized, highly wettable fibers arranged to provide capillary pore sizes and a degree of wettability ideally suited to wick visco-elastic fluids. Stabilization may be accomplished by the use of liquid binders, binder fibers, thermally, or in any other method known to those skilled in the art. When exposed to a visco-elastic fluid or fluid simulant, these materials demonstrate improved fluid distribution performance for distance wicked, wicking rate and amount of fluid moved. The pore characteristics are stable, whether dry or wet, with minimal, preferably less than about 25%, more particularly 20%, and still more particularly 15%, swelling or collapse when wetted with the visco-elastic fluid simulant. All of these properties are critical to the overall performance of distribution materials placed in the target area of personal care products such as feminine hygiene products.

Current fluid transfer delay layers employed in personal care absorbent articles allow transfer of fluid from the fluid intake/distribution layer to the pad layer resulting in fluid saturation levels of essentially 0.86/g/g/in in the intake distribution layer and/or fluid saturation levels of 0.067 g/g/in the pad layer. Personal care articles which demonstrate relatively high levels of saturation in the intake/distribution layer and relatively low levels of saturation in the pad layer as measured using the flat system testing procedure often have relatively high intake times and high rewet values such as those measured with the intake/rewet test. The fluid transfer delay layer employed in the personal care absorbent article of this invention enables fluid transfer from the intake/distribution layer to the pad layer while still allowing fluid distribution by the fluid intake/distribution layer along the machine direction of the article. This results in a fluid saturation level of less than or equal to about 0.86 g/g/in in the fluid intake/distribution material and/or a fluid saturation level essentially equal to or greater than 0.06 g/g/in in the pad layer. Fluid transfer delay is generally accomplished by the fluid transfer delay layer having a lower density than the fluid intake/distribution layer.

BRIEF DESCRIPTION OF THE DRAWINGS

These and other objects and features of this invention will be better understood from the following detailed description taken in conjunction with the drawings wherein.

DESCRIPTION OF PREFERRED EMBODIMENTS

Definitions

Figure 1:
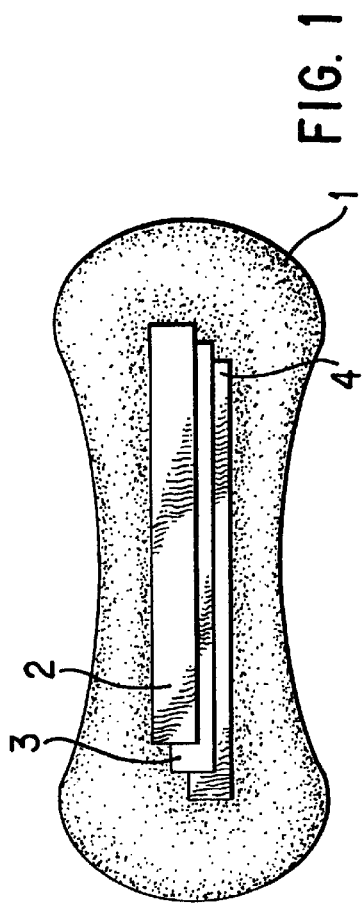
FIG. 1 is a diagram showing a multiple-layered personal care absorbent article in accordance with one embodiment of this invention.

As used herein, the following terms have the definitions ascribed to them.

The term "disposable" includes being disposed of after use and not intended to be washed and reused.

The term "hydrophilic" describes fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials can be provided by a CAHN SFA-222 Surface Force Analyzer System, or a substantially equivalent system. When measured with this system, fibers having contact angles less than 90° are designated "wettable" or hydrophilic, while fibers having contact angles equal to or greater than 90° are designated "non-wettable" or hydrophobic.

As used herein, the term "nonwoven fabric or web" means a web having a structure of individual fibers or threads which are interlaid, but not in an identifiable manner, as in a knitted fabric. Nonwoven fabrics or webs have been formed from many processes such as, for example, meltblowing processes, spunbonding processes, and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91).

As used herein, the term "spunbonded fibers" refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., U.S. Pat. No. 3,692,618 to Dorschner et al., U.S. Pat. No. 3,802,817 to Matsuki et al., U.S. Pat. No. 3,338,992 and U.S. Pat. No. 3,341,394 to Kinney, U.S. Pat. No. 3,502,763 to Hartmann, and U.S. Pat. No. 3,542,615 to Dobo et al. Spunbond fibers are generally not tacky when they are deposited onto a collecting surface. Spunbond fibers are generally continuous and have average diameters (from a sample of at least 10) larger than 7 microns, more particularly, between about 10 and 20 microns. The fibers may also have shapes such as those described in U.S. Pat. No. 5,277,976 to Hogle et al., U.S. Pat. No. 5,466,410 to Hills, and U.S. Pat. No. 5,069,970 and U.S. Pat. No. 5,057,368 to Largman et al., which describe hybrids with unconventional shapes.

As used herein, the term "meltblown fibers" means fibers formed by extruding a molten thermoplastic material through a plurality of fine, usually circular, die capillaries as molten threads or filaments into converging high velocity, usually hot, gas (for example, air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al. Meltblown fibers are microfibers which may be continuous or discontinuous, are generally smaller than 10 microns in average diameter, and are generally tacky when deposited onto a collecting surface.

As used herein, the term "polymer" generally includes, but is not limited to, homopolymers, copolymers, such as for example, block, graft, random and alternating copolymers, terpolymers, etc., and blends and modifications thereof. Furthermore, unless otherwise specifically limited, the term "polymer" shall include all possible geometric configurations of the molecule. These configurations include, but are not limited to, isotactic, syndiotactic and random symmetries.

As used herein, the term "machine direction" or "MD" means the length of a fabric in the direction in which it is produced. The term "cross machine direction" or "CD" means the width of fabric, that is a direction generally perpendicular to the MD.

As used herein, the term "monocomponent" fiber refers to a fiber formed from one or more extruders using only one polymer. This is not meant to exclude fibers formed from one polymer to which small amounts of additives have been added for coloration, anti-static properties, lubrication, hydrophilicity, etc. These additives, for example titanium dioxide for coloration, are generally present in an amount less than about 5 weight percent and more typically about 2 weight percent.

As used herein, the term "conjugate fibers" refers to fibers which have been formed from at least two polymers extruded from separate extruders but spun together to form one fiber. Conjugate fibers are also sometimes referred to as multicomponent or bicomponent fibers. The polymers are usually different from each other though conjugate fibers may be monocomponent fibers. The polymers are arranged in substantially constantly positioned distinct zones across the cross-section of the conjugate fibers and extend continuously along the length of the conjugate fibers. The configuration of such a conjugate fiber may be, for example, a sheath/core arrangement wherein one polymer is surrounded by another, or may be a side-by-side arrangement, a pie arrangement, or an "islands-in-the-sea" arrangement. Conjugate fibers are taught by U.S. Pat. No. 5,108,820 to Kaneko et al., U.S. Pat. No. 4,795,668 to Krueger et al., U.S. Pat. No. 5,540,992 to Marcher et al., and U.S. Pat. No. 5,336,552 to Strack et al. Conjugate fibers are also taught by U.S. Pat. No. 5,382,400 to Pike et al., and may be used to produce crimp in the fibers by using the differential rates of expansion and contraction of the two (or more) polymers. Crimped fibers may also be produced by mechanical means and by the process of German Patent DE 2513251A1. For two component fibers, the polymers may be present in ratios of 75/25, 50/50, 25/75 or any other desired ratios. The fibers may also have shapes such as those described in U.S. Pat. No. 5,277,976 to Hogle et al., U.S. Pat. No. 5,466,410 to Hills and U.S. Pat. No. 5,069,970 and U.S. Pat. No. 5,057,368 to Largman et al., which describe fibers with unconventional shapes.

As used herein, the term "biconstituent fibers" refers to fibers which have been formed from at least two polymers extruded from the same extruder as a blend. Biconstituent fibers do not have the various polymer components arranged in relatively constantly positioned distinct zones across the cross-sectional area of the fiber and the various polymers are usually not continuous along the entire length of the fiber, but rather typically form fibrils or protofibrils which start and end at random. Biconstituent fibers are sometimes also referred to as multiconstituent fibers. Fibers of this general type are taught, for example, by U.S. Pat. Nos. 5,108,827 and 5,294,482 to Gessner.

As used herein, the term "bonded carded web" refers to webs made from staple fibers which are sent through a combing or carding unit, which breaks apart and aligns the staple fibers in the machine direction to form a generally machine direction-oriented fibrous nonwoven web. Such fibers are usually purchased in bales which are placed in a picker which separates the fibers prior to the carding unit. Once the web is formed, it is then bonded by one or more of several known bonding methods. One such bonding method is powder bonding, wherein a powdered adhesive is distributed through the web and then activated, usually by heating the web and adhesive with hot air. Another suitable bonding method is pattern bonding, wherein heated calender rolls or ultrasonic bonding equipment are used to bond the fibers together, usually in a localized bond pattern, though the web can be bonded across its entire surface, if so desired. Another suitable and well-known bonding method, particularly when using bicomponent staple fibers, is through-air bonding.

As used herein, the term "airlaying" means a process by which a fibrous nonwoven layer can be formed. In the airlaying process, bundles of small fibers having typical lengths ranging from about 6 to about 19 mm are separated and entrained in an air supply and then deposited onto a forming screen, usually with the assistance of a vacuum supply. The randomly deposited fibers then are bonded to one another using, for example, hot air or a spray adhesive.

As used herein, the term "personal care product" or "personal care absorbent product" means diapers, training pants, absorbent underpants, adult incontinence products, bandages and feminine hygiene products.

Test Procedures

Wicking Time and Horizontal Liquid Flux of an Absorbent Structure

A sample strip of material approximately one inch (2.5 cm) by eight inches (20 cm) is placed horizontally such that when the sample strip is positioned in a liquid reservoir at the beginning of the test, the sample strip will just touch the liquid surface. The relative humidity is maintained at about 90% to about 98% during the evaluation. The sample strip is placed next to a large (effectively infinite) amount of liquid and a stopwatch started as soon as the edge of the sample strip touches a surface of the solution. The horizontal distance of the liquid front traveling along the sample strip and the liquid weight absorbed by the sample strip at various times are recorded. The weight of the liquid absorbed by the sample strip from the beginning of the evaluation to about a half inch (1.3 cm), one inch, two inches (5 cm) and three inches (7.6 cm) is also determined from the data. The liquid used in this testing is a fluid designed to simulate the visco-elastic and other properties of menses and is made according to a procedure discussed hereinbelow.

Intake/Rewet Test

This test is used to determine the intake time of a known quantity of fluid into a material and/or material system. The test apparatus consists of a rate block, a funnel and a timer or stopwatch.

For measuring fluid intake time, a material system is assembled as it would be in finished product form according to finished product dimensions:

| | |
|---|---|
| Cover - (QUEST) | 3" × 6" |
| Intake/Distribution layer (200 gsm, 0.12 g/cc airlaid) | 1.5" × 6" |
| Transfer delay layer | 3" × 6" |
| Pad layer (fluff or airlaid) | 3" × 6" |

The system is assembled, the cover placed over the absorbent and the rate block placed on top of the two materials. For our work, 4 ml of an artificial menses fluid prepared as described hereinbelow or 6 ml of Z-date artificial menstrual fluid was delivered into the test apparatus funnel and a timer was initiated. The fluid moves from the funnel into a capillary where it is delivered to the material or material system. The timer is stopped when all the fluid is absorbed into the material or material system as observed from the chamber in the test apparatus. The intake time for a known quantity of test fluid is recorded for a given material or material system. This value is a measure of a material or materials system absorbency with lower intake time representing more absorbent systems. Five repetitions are performed to determine average intake time.

The rewet portion of this test is used to determine the amount of fluid that will return to the surface of a cover when a load is applied. The amount of fluid that comes back through the surface is called the rewet value. The more fluid that returns to the surface, the larger the rewet value, while the smaller the amount of fluid that returns to the surface, the lower the rewet value. Lower rewet values are associated with a dryer material and hence a dryer product. In considering rewet, three properties are important:

intake—if the material/system does not have good intake, then fluid can rewet;

ability of an absorbent to hold fluid—the more the absorbent holds onto the fluid, the less fluid is available for rewet; and flowback—the more the cover prohibits fluid from coming back through the cover, the lower the rewet.

After the system is insulted during the intake portion, it is allowed to interact with the system for 1 minute as the rate block rests on top of the materials. The material system is placed onto a closed bag, partially filled with saline solution. The fluid back is positioned on top of a lab jack. Pieces of blotter paper are weighed and placed on top of the material system. The bag with the material system is raised against a fixed acrylic plate using the lab jack until a total of 1 psi is applied. The pressure is held fixed for 3 minutes after which the pressure is removed and the blotter paper is weighed. The blotter paper should retain any fluid that is transferred to it from the cover/absorbent system. The difference in weight between the original blotter and the blotter after the absorption experiment is the rewet value. The individual material components are then weighed to determine fluid partitioning after the pressure is applied.

Flat System Testing Procedure

The purpose of this procedure is to determine the fluid handling characteristics of various absorbent systems through analysis of stain length, saturation capacity, and the fluid loading of the system components. The equipment required includes hourglass-shaped acrylic plates (with a 0.25 inch hole in the center) weighing approximately 330 grams, syringes, one-eighth inch I.D. Tygon tubing, pipette pump, menses simulant, and a laboratory balance (accurate to 0.00 g).

Samples to be tested are cut to a desired shape (currently 1.5 inches by 5.5 inches for fluid intake/distribution layers, 1.75 inches by 5.5 inches for transfer delay layers, and 200 mm long hourglass shape for pad layers). The 5.5 inch layers are marked into 1.1 inch sections and the pad layer is marked into sections corresponding to the marks on the 5.5 inch layers when they are centered on the pad layer. Each component is weighed and the weight recorded. The individual components are assembled into a desired component system maintaining the marked sections aligned and one end is labeled as the top. Syringes are filled with menses simulant and Tygon tubing attached to the syringes. The syringes are placed in a pipette pump which is programmed to deliver a given amount of simulant, currently 30 cc syringes dispensing 10 ml of simulant in one hour. With the open ends of the tubing placed in a beaker, the tubing is primed by running the pump until all air is out of the tubing and simulant is exiting the tubing at the insult end. The component systems to be tested are placed near the pipette pump and a two inch by six inch piece of 25 gsm, 10 d BCW is placed on top of the center of the system over which an acrylic plate is placed, also centered on top of the system. The free end of one tubing is inserted into the hole in the acrylic plate and the pipette pump started to begin the insults. At the end of the insult period, the tubing and acrylic plates are removed. The BCW is then carefully removed without moving the underlying layers and discarded. Each layer is then individually weighed and the weight recorded. Then, beginning at the end labeled as the top, each marked section is cut and weighed. The stain length for each layer is measured and recorded and the data entered into a spreadsheet for graphing and analysis. The fluid loading (g/g) is calculated by dividing the amount of fluid absorbed in a material by the dry weight of the material. The fluid saturation is calculated by dividing the fluid loading by the stain length.

Menses Simulant Preparation

The artificial menses fluid used in the testing was made from blood and egg white by separating the blood into plasma and red cells and separating the white into thick and thin portions, where "thick" means it has a viscosity after homogenization above about 20 centipoise at 150 $\sec^{-1}$, combining the thick egg white with the plasma and thoroughly mixing, and finally adding the red cells and again thoroughly mixing.

Blood, in this case defibrinated swine blood, was separated by centrifugation at 3000 rpm for thirty minutes, although other methods or speeds and times may be used if effective. The plasma was separated and stored separately, the buffy coat removed and discarded, and the packed red blood cells stored separately as well.

Eggs, in this case jumbo chicken eggs, were separated, the yolk and chalazae discarded and the egg white retained. The egg white was separated into thick and thin portions by straining the white through a 1000 micron nylon mesh for about three minutes, and the thinner portion discarded. Note that alternative mesh sizes may be used and the timer method may be varied provided the viscosity is at least that required. The thick portion of egg white which was retained on the mesh was collected and drawn into a 60 cc syringe which was then placed on a programmable syringe pump and homogenized by expelling and refilling the contents five times. In this case, the amount of homogenization was controlled by the syringe pump rate of about 100 ml/min, and the tubing inside diameter of about 0.12 inches. After homogenizing, the thick egg whites had a viscosity of at least 20 centipoise at 150 $\sec^{-1}$ and were then placed in the centrifuge and spun to remove debris and air bubbles at about 3000 rpm for about 10 minutes, although any effective method to remove debris and bubbles may be used.

After centrifuging, the thick, homogenized egg white, which contains ovamucin, was added to a 300 cc FEN-WAL® Transfer Pack using a syringe. 60 cc of the swine plasma were then added to the Transfer Pack which was clamped, all air bubbles removed, and placed in a Stomacher lab blender where it was blended at normal (or medium) speed for about two minutes. The Transfer Pack was then removed from the blender, 60 cc of swine red blood cells added, and the contents mixed by hand kneaded for about two minutes or until the contents appeared homogenous. A hematocrit of the final mixture shows a red blood cell content of about 30 weight percent and generally should be at least within a range of 28–32 weight percent for artificial menses made according to this example. The amount of egg white is about 40 weight percent.

The ingredients and equipment used in the preparation of artificial menses are readily available. Below is a listing of sources for the items used in the example, though of course other sources may be used provided they are approximately equivalent.

Blood (swine): Cocalico Biologicals, Inc., 449 Stevens Rd., Reamstown, Pa. 17567, (717) 336–1990.

Fenwal® Transfer pack container, 300 ml, with coupler, code 4R2014: Baxter Healthcare Corporation, Fenwal Division, Deerfield, Ill. 60015.

Harvard Apparatus Programmable Syringe Pump Model No. 55–4143: Harvard Apparatus, South Natick, Mass. 01760.

Stomacher 400 laboratory blender Model No. BA 7021, Ser. No. 31968: Seward Medical, London, England, United Kingdom.

1000 micron mesh, Item No. CMN-1000-B: Small Parts, Inc., PO Box 4650, Miami Lakes, Fla. 33014-0650, 1-800-220-4242.

Hemata Stat-II device to measure hemocrits, Ser. No. 1194Z03127: Separation Technology, Inc., 1096 Rainer Drive, Altamont Springs, Fla. 32714.

Contact Angle Measurements

Static contact angle measurements were conducted using artificial menses on film surfaces. These surfaces were either treated or unmodified as described in this work. Drops which measured 0.5 to 2 mm in height were applied to the surface of the film with a tapered tip using a syringe and a programmable pump (Harvard Apparatus PHD 2000). A Leica Wild M3Z stereoscopic microscope was tilted on edge to view the drop of fluid as it was applied to the film surface. A Sony DKC-5000 digital photocamera 3CCD recorded the application of the fluid to the surface. Later, contact angle (θ) measurements were made on the individual drops of fluid as they contacted the surface using an image analysis program. Five measurements of contact angle were made on each side of the drop and averaged. A total of five to ten drops were measured for each film and averaged.

Pore Size Measurements

A pore radius distribution chart shows pore radius in microns in the x-axis and pore volume (volume absorbed in cc of liquid/gram of dry sample at that pore interval) in the y-axis. The peak pore size ($r_{peak}$) was extracted from this chart by measuring the value of pore radius at the largest value of volume absorbed from the distribution of pore volume (cc/g) vs. pore radius. This distribution is determined by using an apparatus based on the porous plate method first reported by Burgeni and Kapur in the Textile Research Journal Volume 37, 356–366 (1967). The system is a modified version of the porous plate method and consists of a movable Velmex stage interfaced with a programmable stepper motor and an electronic balance controlled by a computer. A control program automatically moves the stage to the desired height, collects data at a specified sampling rate until equilibrium is reached, and then moves to the next calculated height. Controllable parameters of the method include sampling rates, criteria for equilibrium and the number of absorption/desorption cycles.

Data for this analysis was collected using mineral oil (Peneteck Technical Mineral Oil) with a viscosity of 6 centipoise manufactured by Penreco of Los Angeles, Calif. in desorption mode. That is, the material was saturated at zero height and the porous plate (and the effective capillary tension on the sample) was progressively raised in discrete steps corresponding to the desired capillary radius. The amount of liquid pulled out from the sample was monitored. Readings at each height were taken every fifteen seconds and equilibrium was assumed to be reached when the average change of four consecutive readings was less than 0.005 g. This method is described in more detail in U.S. Pat. No. 5,679,042 to Varona.

Material Caliper (thickness)

The caliper of a material is a measure of thickness and is measured at 0.05 psi with a Starret-type bulk tester, in units of millimeters or inches. The foot of the bulk tester used in these studies is a small acrylic cylinder measuring 3" wide by 0.5 inches in thickness.

Permeability

Permeability is obtained from a measurement of the resistance by the material to the flow of liquid. A liquid of known viscosity is forced through the material of a given thickness at a constant flow rate and the resistance to flow, measured as a pressure drop is monitored. Darcy's Law is used to determine permeability as follows:

Permeability=[flow rate x thickness x viscosity/pressure drop] Equation (1) where the units are:

| permeability: | $cm^2$ or darcy | 1 darcy = $9.87 \times 10^{-9}$ $cm^2$ |
|---|---|---|
| flow rate: | cm/sec | |
| viscosity: | pascal-sec | |
| pressure drop: | pascals | |

The apparatus consists of an arrangement wherein a piston within a cylinder pushes liquid through the sample to be measured. The sample is clamped between two aluminum cylinders with the cylinders oriented vertically. Both cylinders have an outside diameter of 3.5", an inside diameter of 2.5" and a length of about 6". The 3" diameter web sample is held in place by its outer edges and hence is completely contained within the apparatus. The bottom cylinder has a piston that is capable of moving vertically within the cylinder at a constant velocity and is connected to a pressure transducer that capable of monitoring the pressure of encountered by a column of liquid supported by the piston. The transducer is positioned to travel with the piston such that there is no additional pressure measured until the liquid column contacts the sample and is pushed through it. At this point, the additional pressure measured is due to the resistance of the material to liquid flow through it.

The piston is moved by a slide assembly that is driven by a stepper motor. The test starts by moving the piston at a constant velocity until the liquid is pushed through the sample. The piston is then halted and the baseline pressure is noted. This corrects for sample buoyancy effects. The movement is then resumed for a time adequate to measure the new pressure. The difference between the two pressures is the pressure due to the resistance of the material to liquid flow and is the pressure drop used in Equation (1). The velocity of the piston is the flow rate. Any liquid whose viscosity is known can be used, although a liquid that wets the material is preferred since this ensures that saturated flow is achieved. The measurements disclosed herein were carried out using a piston velocity of 20 cm/min, mineral oil (Peneteck Technical Mineral Oil manufactured by Penreco of Los Angeles, Calif.) of a viscosity of 6 centipoise.

Alternatively, permeability can be calculated from the following equation:

$$\text{Permeability} = 0.051 * R * (1-\text{Porosity}) * (\text{Porosity}/(1-\text{Porosity}))^{2.75} \quad \text{Equation (2)}$$

where R=fiber radius and $$\text{Porosity} = 1 - (\text{web density/fiber density}) \quad \text{Equation (3)}$$

Reference for Equation (2) can be found in the article "Quantification of Unidirectional Fiber Bed Permeability" by J. Westhuizen and J. P. Du Plessis in the *Journal of Composite Materials*, 28(7), 1994. Note that the equations show that permeability can be determined if fiber radius, web density and fiber density are known.

Conductance is calculated as permeability per unit thickness and gives measure of the openness of a particular structure and, thus, an indication of the relative ease at which a material will pass liquid. The units are darcies/mil.

This invention relates to personal care absorbent articles such as disposable sanitary napkins, diapers, incontinence garments, and the like which utilize a class of distribution materials composed of stabilized, highly wettable fibers arranged to provide capillary pore sizes and a degree of wettability ideally suited to wick visco-elastic fluids coupled with a transfer delay material having characteristics which enhance the performance of the distribution materials. Stabilization of the distribution materials may be accomplished by the use of liquid binders, binder fibers, thermally, or in any other method known to those skilled in the art. When exposed to a visco-elastic fluid or fluid simulant, the distribution materials demonstrate improved fluid distribution performance for distance wicked, wicking rate and amount of fluid moved. In addition, the fluid transfer delay materials enable the use of the thick pad layers present in certain of the absorbent articles for fluid storage by reducing the saturation level of the distribution materials at which fluid in the distribution materials is transported from the distribution materials into the thick pad layers. The pore characteristics of the distribution materials are stable, whether dry or wet with minimal, preferably less than about 25%, more particularly 20% and still more particularly 15%, swelling or collapsed when wetted with the visco-elastic fluid simulant. All of these properties are critical to the overall performance of distribution materials placed in the target area of personal care absorbent articles such as feminine pads.

Fluid distribution capability requires the appropriate capillary pore structure within a specified range of wettability for the fluid of interest. Distribution materials have been developed using several technology approaches that demonstrate the underlying material characteristics needed for favorable performance. Examples of such materials follow.

EXAMPLE 1

In this example, the distribution material consists of about 80 weight percent fluff pulp (Rayonier R-9401 mercerized southern soft wood roll pulp) and about 20 weight percent Danaklon shortcut (5 mm) 2.2 denier polyethylene/polypropylene sheath/core conjugate binder fiber with an S2/B2/39 finish. This finish is advertised as remaining hydrophilic after repeated insults. The material is produced at three different densities: 0.05 g/cc, 0.1 g/cc and 0.2 g/cc at a basis weight of 100 to 250 gsm.

The materials were tested according to the horizontal wicking test which was repeated for a total of three tests using one inch by eight inch samples. Table 1 shows the results where weight is given in grams of retained fluid, time in seconds, and "DNR" means "did not reach."

TABLE 1

|  |  | Rep 1 | | Rep 2 | | Rep 3 | |
|---|---|---|---|---|---|---|---|
|  | (Inches) | Wt. (g) | Time(s) | Wt. (g) | Time(s) | Wt. (g) | Time(s) |
| 0.05 g/cc | 0.5 | 1.26 | 50 | 1.15 | 50 | 1.13 | 54 |
|  | 1.0 | 1.80 | 161 | 1.77 | 170 | 1.55 | 170 |
|  | 2.0 | 1.56 | 633 | 1.71 | 611 | 1.48 | 714 |
|  | 3.0 | 1.02 | DNR | 0.89 | DNR | 0.72 | DNR |
| 0.1 g/cc | 0.5 | 0.86 | 20 | 0.68 | 24 | 0.76 | 18 |
|  | 1.0 | 1.14 | 155 | 1.07 | 123 | 1.03 | 139 |
|  | 2.0 | 0.95 | 811 | 0.91 | 868 | 0.9 | 810 |
|  | 3.0 | 0.32 | DNR | 0.16 | DNR | 0.23 | DNR |
| 0.2 g/cc | 0.5 | 0.79 | 56 | 0.83 | 43 | 0.73 | 56 |
|  | 1.0 | 1.11 | 253 | 1.03 | 174 | 0.98 | 245 |
|  | 2.0 | 0.62 | DNR | 0.96 | 1074 | 0.76 | DNR |
|  |  |  |  | 0.21 | DNR |  |  |

The distribution material is produced by the Dan-Web airlaying process. However, any other satisfactory procedure known to those skilled in the art may be used to produce the material. Samples tested for pore volume distribution show that as density is lowered and pore size is increased, wicking performance is greatly improved.

EXAMPLE 2

In this example, the distribution materials are bonded carded webs consisting of 100 weight percent eccentric sheath/core conjugate fibers of polyethylene and polypropylene available from the Chisso Chemical Company of Japan. The fibers have a finish known as HR6 applied to them. Table 2, hereinbelow, shows the wicking results for a 0.028 g/cc sample, a 0.068 g/cc sample and a 0.028 g/cc sample in which the fibers were oriented in the carding process. The distance is given in inches, the weight in grams and the time in minutes and seconds as indicated. The results of pore volume distribution tests on this material show that when a high percentage of the pore volume has pores that range from about 200 to about 400 microns, better wicking results are achieved.

TABLE 2

| Density | Distance | Weight | Time |
|---|---|---|---|
| 0.028 g/cc | 1.0 | 1.7 | 50 sec. |
|  | 2.0 | 1.1 | 10 min. |
|  | 3.0 | 0.9 | 17 min. |
| 0.068 g/cc | 1.0 | 0.6 | 1.5 min. |
|  | 2.0 | 0.1 | DNR |
| 0.028 g/cc oriented | 1.0 | 1.7 | 1 min. |
|  | 2.0 | 1.2 | 6.6 min. |
|  | 3.0 | 0.9 | 18 min. |
|  | 4.0 | 0.1 | 20+ min. |

The distribution material of this invention should wick the artificial menses fluid according to the horizontal wicking test a distance of an inch (2.5 cm) in less than about 1.5 minutes to be successful. Materials meeting this performance criteria generally have a pore size distribution with a high percentage (usually more than 50%, more particularly more than 60% and still more particularly more than 70%) of pore diameters between about 80 and 400 microns and a density below about 0.15 g/cc. It is believed that increasing the wettability of the pore surface results in greater wicking driving forces which can maintain liquid movement in smaller pores with higher resistive forces.

Personal care absorbent articles of this invention have been designed to have controlled final liquid storage in a centralized region along the length of the pad. This functional behavior is highly desirable for preventing side leakage which is a dominant form of leakage for feminine pads. This storage behavior is achieved by a layered absorbent design that can include three or more layers. The bottom-most layer, that is, the layer furthest from a wearer, has larger x-y dimensions than the other layers that are on top of it. This creates a raised topography design that increases the probability that menses from the wearer will land on the narrow strip as shown in FIG. 1. FIG. 1 shows a multiple layer design having a bottom-most layer 1, a top fluid intake layer 2, a fluid distribution layer 3 disposed below the fluid intake layer 2, and an intermediate layer 4 disposed between the fluid distribution layer 3 and the bottom-most layer 1.

The fluid intake layer is the layer closest to a wearer and has a low density ranging from about 0.02–0.06 g/cc and a basis weight from about 25 gsm to about 125 gsm. This results in pore sizes ranging from 80 microns to 1000 microns in diameter which are well suited to intake viscous menses fluid. The top or intake layer can be produced with a range of technologies. Nonexclusive examples include 100 weight percent synthetic fibers in a bonded carded web or an airlaid mixture of cellulosic and synthetic binder fibers.

The layer below the top layer is designed to distribute and retain fluid and, as such, is called the distribution layer or strip. It has a density range from about 0.1 g/cc to about 0.2 g/cc but must be a higher density than the intake layer. This increased density is believed to help desorb the intake layer into the distribution layer. The distribution layer should have a basis weight from about 175 gsm to about 300 gsm and have an average pore size of about 40–500 microns in diameter. Materials suitable for this layer include airlaid materials that blend high levels of cellulosic fibers (80–95 weight percent) with synthetic binder fibers (5–20 weight percent) which stabilize the web performing this distribution function, provided, however, that the fibers that make up this layer are highly wettable. The bottom or pad shaping layer has a lower density than the distribution layer. Its primary function is to facilitate body fit, provide comfort to the wearer, and to provide additional coverage. Its density ranges from about 0.03 g/cc to about 0.10 g/cc so that it does not readily desorb the distribution layer resulting in most fluid remaining in the distribution layer. In some designs, the pad shaping layer can be an airlaid web with 80–90 weight percent cellulosic pulp fluff blended with 10–20 weight percent synthetic binder fiber. While its primary purpose is pad shaping, this layer can accept liquid from the distribution strip, particularly when the distribution strip is highly loaded with liquid.

It should be noted that though the invention is referred to as having "layers," this does not mean that separate materials must be produced and laminated together. The term "layers" is meant to also include a single monolithic material wherein the properties vary within it in such a manner as to satisfy the functional and physical characteristics of this invention. Thus, a material produced in a single step process and having, for example, characteristics varying from top to bottom regions in such a way as to satisfy the requirements of the invention, is contemplated to be within the claims.

Disposed between the fluid intake/distribution layers 2, 3 and the pad layer 1 is intermediate layer 4 which acts to delay fluid transfer from the fluid intake/distribution layer 2, 3, and is hereinafter referred to as a fluid transfer delay layer. In this case, fluid intake layer 2 provides the fluid intake function while fluid distribution layer 3 is a higher density distribution strip. Fluid transfer delay layer 4 has a lower density than the fluid distribution layer 3, thereby providing a delay in fluid transfer to the wider and thicker pad shaping layer 1 which also provides comfort and thickness requirements.

The center filling platform for personal care absorbent products in accordance with one embodiment of this invention uses an airlaid component to desorb the cover material and hold the majority of fluid therein. With the high loadings occurring during overnight use, the basis weight of the airlaid would, of necessity, have to be very high and expensive in order to get the capacity needed to hold the majority of the fluid. The pad layer of this type of product is a thick maxipad having a 600 gsm fluff pad and a 600 gsm fluff insert. Because this fluff material has to be present in the product for aesthetic and pad shaping reasons, it is ideal to utilize the capacity in that fluff. The transfer delay material layer currently in use in such products allows transfer of the fluid from the fluid intake/distribution layer at about an 80% saturation level of the distribution layer. By enabling fluid transfer from the distribution layer at a lower percentage saturation level and utilizing the capacity of the fluff in the pad layer, it is possible to provide a product capable of handling the high loadings which occur during night time usage of the products.

The fluid transfer delay layer for personal care absorbent products in accordance with this invention is designed to promote the transfer of fluid from the fluid intake/distribution layer(s) to the pad layer while still allowing fluid distribution by the fluid intake/distribution layer along the machine direction of the article. This results in saturation levels of less than or equal to about 0.86 g/g/in of fluid in the intake/distribution layer(s) and/or greater than 0.06 g/g/in. of fluid in the pad layer.

Delay of fluid transfer in the personal care absorbent products of this invention is achievable by controlling the density of the transfer delay material such that it has a lower density than the layer above it. While material density is one way to cause the transfer of fluid to be delayed to the lower layer, other material attributes can also cause delay of fluid transfer. Other material candidates that are effective at causing delay include nonwovens such as spunbond, conjugate spunbond, or bonded carded webs. Apertured films can also be used to supply this function in an absorbent system.

In order to enable the transfer of fluid from the fluid intake/distribution layer to the pad layer, in accordance with one preferred embodiment of this invention, the fluid transfer delay layer forms an open area. Such open area can be provided by any number of techniques known to those skilled in the art including aperturing of the fluid transfer delay layer, slitting of the fluid transfer delay layer, and/or cutting of the fluid transfer delay layer. These open areas may be discrete windows cut into the ends of the transfer delay layer, or they may be uniform aperturing or brick slitting of the material. In addition, the open areas may be zoned such as by zone aperturing on the ends of the transfer delay layer.

Alternatively, the transfer delay layer may be cut into a shape so that it is zoned in regions, for example, diamond shaped, where the transfer delay layer is as wide as the fluid intake/distribution layer in the centralized insult zone but then tapers in width to a point under the ends of the fluid intake/distribution layer.

In accordance with one preferred embodiment of this invention, the transfer delay layer includes a wettability gradient where the center of the transfer delay layer beneath the centralized fluid intake zone is non-wettable or less wettable than the ends of the transfer delay layer.

In accordance with a particularly preferred embodiment of this invention, the fluid transfer delay layer comprises a nonwoven web having a basis weight in the range of about 0.5 osy (17 gsm) to about 1.0 osy (34 gsm) and comprises polyolefin fibers having a denier in the range of about 2.0 to about 3.0. In accordance with a particularly preferred embodiment of this invention, the nonwoven web is a spunbond. Any wettable agents known to those skilled in the art may be employed in connection with the material of this invention.

EXAMPLE 3

Systems of materials were created to demonstrate the effects of transfer delay characteristics on fluid distribution and transfer and more specifically, its impact on absorbency and dryness properties. The following transfer delay materials were prepared and evaluated:

| | |
|---|---|
| Control | 2.7 dpf, 0.8 osy Spunbond - Untreated |
| Specimen A | 2.7 dpf, 0.8 osy Spunbond with 0.4% Ahcovel |
| Specimen B | 2.7 dpf, 0.4 osy Spunbond - Untreated |
| Specimen C | No transfer delay |
| Specimen D | 2.7 dpf, 0.6 osy Spunbond - Untreated |
| Specimen E | Pin apertured 1 mil PE Edison LDPE XP-746A |
| Specimen F | 2.7 dpf, 0.8 osy Spunbond with 0.1% Ahcovel |
| Specimen G | 2.7 dpf, 0.8 osy Spunbond with 0.2% Ahcovel |
| Specimen H | 2.7 dpf, 0.8 osy Spunbond with 0.36% Ahcovel |
| Specimen I | 2.7 dpf, 0.8 osy Spunbond with 0.67% Ahcovel |

Spunbond fabrics described in Example 3 were produced using 96 weight % of E5D47 polypropylene (Union Carbide) and approximately 4% additive SCC(25950 #7 Rose). The fiber density for all webs in the Examples was approximately 0.91 g/cc. The thickness of the spunbond fabrics for the preceding specimens were aproximately 0.006 inches for the 0.4 osy specimens and approximately 0.010 inches for the 0.6 and 0.8 osy specimens.

Figure 2:
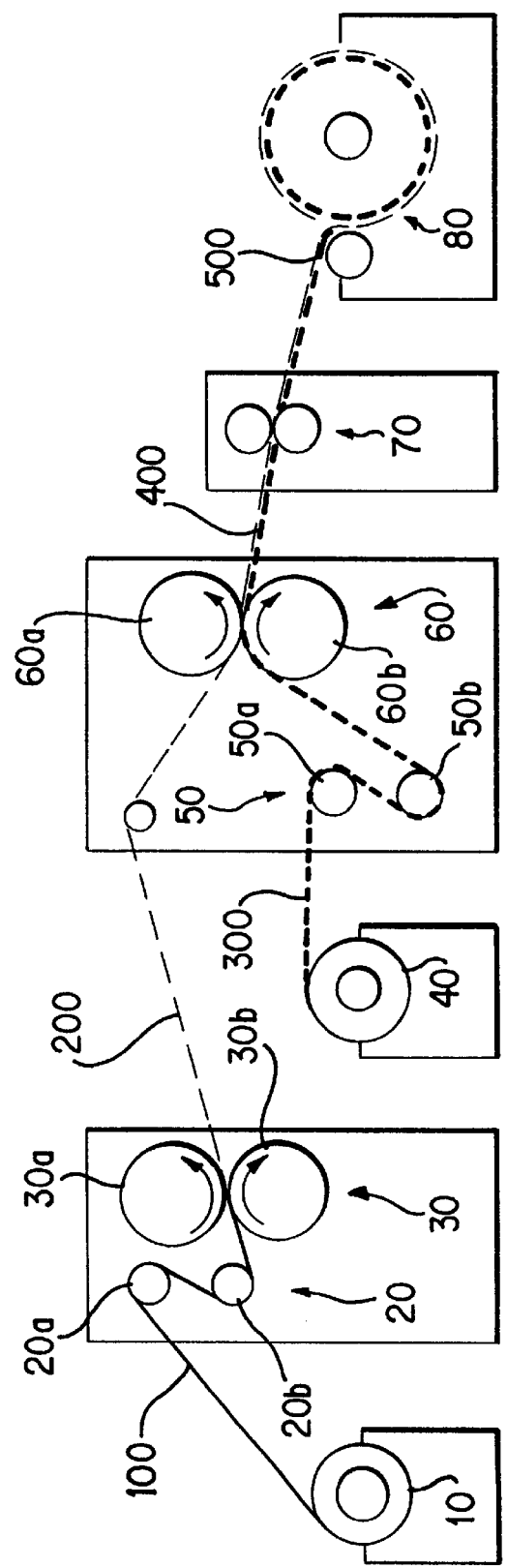
FIG. 2 is a schematic diagram showing a process for aperturing a film material for use in a fluid absorbent material in accordance with one embodiment of this invention.

Aperturing of Specimen E was carried out in accordance with the process shown in FIG. 2. In particular, the films were apertured mechanically in nip 30. The aperturing process comprises controlling the feed rate of the film 100 separate from the aperturing rate. The feed and the aperturing rate are controlled by the drive system 20. The aperturing rate is controlled by the rotation rate of the rolls in the aperturing nip 30, pattern roll 30a and anvil roll 30b. The speed of the film 100 is slower than the peripheral speed of pattern roll 30a and faster than the peripheral speed of anvil roll 30b.

Film 100 is apertured under tension to minimize wrinkling of the film from a driven unwind 10 slower than the speed that drive system 20 and idler rolls (not shown) pull the film 100. The drive unit comprises "S" wrapping the film 100 between a driven rubber roll 20a and a steel roll 20b to control the entrance speed of the film into aperturing nip 30. Pattern roll 30a and anvil roll 30b contact one another and form nip 30 therebetween. Pattern roll 30a and anvil roll 30b rotate in opposite directions. Each of pattern roll 30a and anvil roll 30b is driven separately. Peripheral speed of pattern roll 30a is set at about 1.3–1.4 times the peripheral speed of anvil roll 30b.

For our work, film 100 was apertured at a speed of 100 feet per minute. Each of pattern roll 30a and anvil roll 30b was made from stainless steel and had an outside diameter of about 24 inches. The rolls were maintained at different temperatures using an internal hot oil system, pattern roll 30a being maintained at a temperature of about 255° F. and anvil roll 30b being maintained at a temperature of about 228° F. Anvil roll 30b had a smooth finish while pattern roll 30a had a plurality of pins positioned to give a desired pattern. The desired pattern had a density of about 93.5 pins per square centimeter (580–603 pins/inches$^2$) and a total contact area of about 37–46%. Each pin had a height of about 0.48 millimeters (0.01–0.022 inches), was tapered about 10°, and was circular in cross section. Because the pins had an apex diameter of about 0.73 millimeters (0.0286 inches), the surface area of the apex was about 0.40 millimeters$^2$ (0.00066 inches$^2$).

As film 100 enters nip 30, it is apertured through the application of heat, shear and pressure by penetrating pins which extend completely through the thickness of film 100. Shear is created by running the pattern roll 30a faster than the anvil roll 30b. The apertured film 200 exits nip 30 under tension and can be directed around an idler roll (not shown) to keep the apertured film 200 from wrinkling as it is separated from pattern roll 30a. These process conditions produce an apertured film having an open area of approximately 28% with an equivalent-circular diameter (ECD) of approximately 600 microns. The remaining portion of FIG. 2 depicts a general process in which apertured film 200 is laminated to a nonwoven web 300 in which the apertured film 200 and nonwoven web 300 pass through nip 60 comprised of a pattern roll 60a and an anvil roll 60b. After lamination, the laminate is collected on spool 80.

The following materials were tested as systems of materials using the intake/rewet test and the flat system test. For the first set of experiments, the intake/distribution layer was a 200 gsm, 0.12 g/cc airlaid with 90% Coosa 0054 pulp and 10% Hoechst-Celanese T-255 conjugate binder fiber while the pad layer was composed of 600 gsm Coosa 0056 pulp with a density of 0.09 g/cc using a Sine Wave Embossed Pattern #C200-M-3558C. The cover was a 1.1 mil low density polyethylene film (XP3134A-Edison Plastics, Newport News, Va.) apertured using the process previously described. This apertured film was point bonded to a 6 dpf, 0.7 osy Chisso through air bonded carded web which had a density of approximately 0.018 g/cc. The Chisso fibers, available from Chisso Corporation, had a surfactant treatment consisting of a wettable finish, HR6. This apertured film and bonded carded web composite cover are also known as QUEST.

Table 3 below shows intake time comparisons of different transfer delay layers when menses simulant is used as the test fluid. The treated 0.8 osy sample and the 0.4 osy spunbond samples effectively reduced intake times to the level of the code without a transfer delay layer (TDL). The results shown in Table 3 were generated using the intake/rewet test (STP 682-W) with 4 ml of menses simulant.

TABLE 3

| Sample | Intake Time |
|---|---|
| Specimen C | 29.57 |
| Control | 39.95 |
| Specimen A | 27.12 |
| Specimen D | 43.21 |
| Specimen B | 28.93 |
| Specimen E | 38.74 |

Table 4 below shows the effects of different transfer delay layers on rewet values when using menses simulant as the test fluid.

TABLE 4

| Sample | Rewet (g) |
|---|---|
| Specimen C | 0.18 |
| Control | 0.88 |
| Specimen A | 0.29 |
| Specimen D | 0.70 |
| Specimen B | 0.17 |
| Specimen E | 0.50 |

The results show that the 0.8 osy treated spunbond or a 0.4 osy spunbond results in rewet values that are comparable to a code without a TDL. In addition, the apertured film code and the 0.6 osy TDL reduce rewet beyond the 0.8 osy control code. The results were generated using the intake/rewet test (STP 682-W) with 4 ml of menses simulant.

Table 5 below shows how stain length (and therefore distribution) and fluid paritioning in the intake/distribution layer and the pad layer can be modified by imparting wettability to the transfer delay layer or reducing its basis weight. The data below was generated with the flat system fluid distribution test using 6 ml of menses simulant and 0.25 psi. As observed from the fluid loading of the intake/distribution layer and the pad layer, one notes that increasing the wettability or decreasing the basis weight of the transfer delay layer decreases the amount of fluid in the intake/distribution layer and increases the amount of fluid in the pad layer. The stain length in the intake distribution layer decreases with increases in wettability or decreases in basis weight of the transfer delay material. Combining these premises, the fluid saturation decreases in the intake/distribution layer and increases in the retention layer with increases in wettability or decreases in basis weight of the transfer delay layer.

TABLE 5

| Sample | Layer | Fluid Loading (g) | Fluid Loading (g/g) | Stain Length (in) | Fluid Saturation (g/g/in) |
|---|---|---|---|---|---|
| Control | Intake/Distribution | 5.83 | 4.72 | 5.50 | 0.86 |
| Control | Pad | 0.33 | 0.05 | 0.75 | 0.067 |
| Specimen A | Intake/Distribution | 4.78 | 3.82 | 4.75 | 0.80 |
| Specimen A | Pad | 1.56 | 0.23 | 2.25 | 0.10 |
| Specimen B | Intake/Distribution | 3.43 | 2.99 | 3.95 | 0.76 |
| Specimen B | Pad | 2.07 | 0.30 | 2.75 | 0.109 |

In summary, currently available materials have an intake/distribution layer saturation of greater than about 0.86 g/g/in and a pad layer saturation of 0.067 g/g/in. Increasing the wettability or decreasing the basis weight of the transfer delay layer in accordance with the absorbent articles of this invention decreases the saturation of the intake/distribution layer below 0.86 g/g/in and increases the level of saturation of the retention material above 0.067 g/g/in. Current systems, which consist of a 2.7 dpf, 0.8 osy nonwettable transfer delay layer, have high intake times and high rewet values due to a higher saturation level of the intake/distribution material. The intake time and rewet values may be decreased through the addition of a wettable or lower basis weight transfer delay layer. The intake times using the transfer delay layers of this invention are reduced because they promote more fluid transfer to the retention material, presumably thus regenerating void volume to accommodate the initial fluid insult. The rewet value is lower due to the decreased saturation of the intake/distribution material which is next to the cover.

In these examples, it was illustrated that the increase in wettability and decrease in basis weight of the transfer delay layer increased fluid transfer and thus reduced saturation level in the intake/distribution material and increased saturation in the retention material.

Mechanistically, it is not specifically the basis weight and wettability that are controlling fluid transfer, but rather the permeability and capillarity.

Capillarity is expressed as follows:

$$\Delta P = 2*\gamma*\cos(\theta)/r$$

where $\gamma$ is the surface tension of the fluid, $\theta$ is the contact angle the fluid makes with a solid surface, and r is the pore radius. Thus, as the surface tension of the fluid increases, the wettability increases, or as the pore size decreases, the capillarity increases.

The other important characteristic of the material is the permeability. For the transfer delay materials exemplified as Specimens A and B, the permeabilities have been measured and $\Delta P/\gamma$ calculated from experimental measurements to define the important characteristics of this invention. Thus one notes from the table, that transfer delay materials with permeability essentially equal to or greater than about 530 darcies or $\Delta P/\gamma$ essentially equal to or greater than 0.0020 microns$^{-1}$ produce the intended results.

TABLE 6

| Specimen | Permeability (Darcies) | Peak Pore Size ($r_{peak}$) (microns) | Contact Angle* ($\theta$) | $\Delta P/\gamma$ (microns$^{-1}$) |
|---|---|---|---|---|
| Control | 519 | 60 | 87 | 0.0018 |
| A | 519 | 60 | 75 | 0.0086 |
| B | 773 | 80 | 87 | 0.0013 |

*Contact angles were measured with menses simulant for 0.5% AHCOVEL ® treatment on a model polyethylene surface (XP3134a, Edison Plastics, Newport News, Virginia) and were compared to an untreated polyethylene surface. The contact angle of the untreated surface was approximately 87 degrees while that of the treated surface was about 75 degrees.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. A personal care absorbent article comprising:
    a fluid intake/distribution layer; and
    a fluid transfer delay layer disposed beneath said fluid intake/distribution layer, said fluid transfer delay layer enabling a transfer of fluid from the fluid intake/distribution layer to a pad layer disposed beneath said fluid transfer delay layer while still allowing fluid distribution by said fluid intake/distribution layer along a machine direction of the article resulting in saturation levels of less than about 0.86 g/g/in of fluid in said fluid intake/distribution layer obtained from a Flat System Testing Procedure;
    wherein the fluid transfer delay layer has one of a permeability greater than about 530 darcies and a capillarity ($\Delta P/\gamma$) greater than about 0.0020 microns$^{-1}$.

2. A personal care absorbent article in accordance with claim 1, wherein the transfer of fluid from the fluid intake/distribution layer to the pad layer results in a fluid saturation level in said pad layer of greater than 0.067 g/g/in obtained from a Flat System Testing Procedure.

3. A personal care absorbent article comprising:

a fluid intake/distribution layer; and a fluid transfer delay layer disposed beneath said fluid intake/distribution layer, said fluid transfer delay layer enabling a transfer of fluid from the fluid intake/distribution layer to a pad layer disposed beneath said fluid transfer delay layer while still allowing fluid distribution by said fluid intake/distribution layer along a machine direction of the article resulting in saturation levels of less than about 0.86 g/g/in of fluid in said fluid intake/distribution layer obtained from a Flat System Testing Procedure;

wherein the fluid transfer delay layer has one of a permeability greater than about 530 darcies and a capillarity ($\Delta P/\gamma$) greater than about 0.0020 microns$^{-1}$;

wherein said fluid transfer delay layer comprises a nonwoven web having a basis weight in a range of about 0.1 osy (3 gsm) to about 1.0 osy (34 gsm) and comprising polyolefin fibers having a denier in a range of about 2.0 to about 3.0.

4. A personal care absorbent article in accordance with claim 3, wherein said nonwoven web is a spunbond.

5. A personal care absorbent article in accordance with claim 4, wherein said fluid transfer delay layer comprises a wettability gradient with a center region of said fluid transfer delay layer being less wettable than a periphery of said fluid transfer delay layer.

6. A personal care absorbent article in accordance with claim 4, wherein said fluid transfer delay layer forms at least one open area.

7. A personal care absorbent article in accordance with claim 6, wherein said at least one open area is formed by one of aperturing, slitting and cutting of said fluid transfer delay layer.

8. A personal care absorbent article in accordance with claim 1, wherein said pad layer comprises fluff and has a basis weight of about 600 gsm.

9. A personal care absorbent article in accordance with claim 1, wherein said fluid intake/distribution layer is an airlaid web in which fluid is distributed from a centrally disposed target area in a machine direction.

10. A personal care absorbent article in accordance with claim 1, wherein said fluid transfer delay layer is a film.

11. A feminine hygiene product comprising:

a backsheet;

a pad layer disposed on a body facing side of said backsheet comprising fluff;

a fluid transfer delay layer disposed on a body facing side of said pad layer, said fluid transfer delay layer being smaller in an x-y plane than said pad layer and enabling a fluid transfer from a fluid intake/distribution layer and thus resulting in the intake/distribution layer having a saturation level of less than about 0.86 g/g/in obtained from a Flat System Testing Procedure;

said fluid intake/distribution layer disposed on a body facing side of said fluid transfer delay layer and being smaller in an x-y plane than said fluid transfer delay layer; and a body side liner disposed on a body facing side of said fluid intake/distribution layer;

wherein the fluid transfer delay layer has one of a permeability greater than about 530 darcies and a capillarity ($\Delta P/\gamma$) greater than about 0.0020 microns$^{-1}$.

12. A feminine hygiene product comprising:

a backsheet;

a pad layer disposed on a body facing side of said backsheet comprising fluff;

a fluid transfer delay layer disposed on a body facing side of said pad layer, said fluid transfer delay layer being smaller in an x-y plane than said pad layer and enabling a fluid transfer from a fluid intake/distribution layer and thus resulting in the intake/distribution layer having a saturation level of less than about 0.86 g/g/in obtained from a Flat System Testing Procedure;

said fluid intake/distribution layer disposed on a body facing side of said fluid transfer delay layer and being smaller in an x-y plane than said fluid transfer delay layer; and a body side liner disposed on a body facing side of said fluid intake/distribution layer;

wherein the fluid transfer delay layer has one of a permeability greater than about 530 darcies and a capillarity ($\Delta P/\gamma$) greater than about 0.0020 microns$^{-1}$;

wherein said fluid transfer delay layer comprises a nonwoven web having a basis weight in a range of about 0.5 osy (17gsm) to about 1.0 osy (34 gsm) and comprising polyolefin fibers having a denier in a range of about 2.0 to about 3.0.

13. A feminine hygiene product in accordance with claim 12, wherein said nonwoven web is a spunbond.

14. A feminine hygiene product in accordance with claim 12, wherein said fluid transfer delay layer comprises a wettability gradient with a center region of said fluid transfer delay layer being less wettable than a periphery of said fluid transfer delay layer.

15. A feminine hygiene product in accordance with claim 11, wherein said fluid transfer delay layer forms at least one open area.

16. A feminine hygiene product comprising:

a backsheet;

a pad layer disposed on a body facing side of said backsheet comprising fluff;

a fluid transfer delay layer disposed on a body facing side of said pad layer, said fluid transfer delay layer being smaller in an x-y plane than said pad layer and enabling a fluid transfer from a fluid intake/distribution layer and thus resulting in the intake/distribution layer having a saturation level of less than about 0.86 g/g/in obtained from a Flat System Testing Procedure;

said fluid intake/distribution layer disposed on a body facing side of said fluid transfer delay layer and being smaller in an x-y plane than said fluid transfer delay layer; and a body side liner disposed on a body facing side of said fluid intake/distribution layer;

wherein the fluid transfer delay layer has one of a permeability greater than about 530 darcies and a capillarity ($\Delta P/\gamma$) greater than about 0.0020 microns$^{-1}$;

wherein said fluid transfer delay layer forms at least one open area; and wherein said at least one open area is formed by one of aperturing, slitting and cutting of said fluid transfer delay layer.

17. In a personal care absorbent article having a fluid intake/distribution layer and a pad layer disposed beneath said fluid intake/distribution layer, the improvement comprising:

a fluid transfer delay layer disposed between said fluid intake/distribution layer and said pad layer, said fluid transfer delay layer enabling a fluid intake time for said fluid intake/distribution layer of less than about 39 seconds obtained from an Intake/Rewet Test;

wherein the fluid transfer delay layer has one of a permeability greater than about 530 darcies and a capillarity ($\Delta P/\gamma$) greater than about 0.0020 microns$^{-1}$.

18. In a personal care absorbent article having a fluid intake/distribution layer and a pad layer disposed beneath said fluid intake/distribution layer, the improvement comprising:

a fluid transfer delay layer disposed between said fluid intake/distribution layer and said pad layer, said fluid transfer delay layer enabling a fluid intake time for said fluid intake/distribution layer of less than about 39 seconds obtained from an Intake/Rewet Test;

wherein the fluid transfer delay layer has one of a permeability greater than about 530 darcies and a capillarity ($\Delta P/\gamma$) greater than about 0.0020 microns$^{-1}$;

wherein said fluid transfer delay layer comprises a nonwoven web having a basis weight in a range of about 0.5 osy (17 gsm) to about 1.0 osy (34 gsm) and comprising polyolefin fibers having a denier in a range of about 2.0 to about 3.0.

19. In a personal care absorbent article having a fluid intake/distribution layer and a pad layer disposed beneath said fluid intake/distribution layer, the improvement comprising:

a fluid transfer delay layer disposed between said fluid intake/distribution layer and said pad layer, said fluid transfer delay layer enabling a rewet value for said fluid intake/distribution layer of less than about 0.88 g obtained from an Intake/Rewet Test;

wherein the fluid transfer delay layer has one of a permeability greater than about 530 darcies and a capillarity ($\Delta P/\gamma$) greater than about 0.0020 microns$^{-1}$.

20. In a personal care absorbent article having a fluid intake/distribution layer and a pad layer disposed beneath said fluid intake/distribution layer, the improvement comprising:

a fluid transfer delay layer disposed between said fluid intake/distribution layer and said pad layer, said fluid transfer delay layer enabling a rewet value for said fluid intake/distribution layer of less than about 0.88 g obtained from an Intake/Rewet Test;

wherein the fluid transfer delay layer has one of a permeability greater than about 530 darcies and a capillarity ($\Delta P/\gamma$) greater than about 0.0020 microns$^{-1}$;

wherein said fluid transfer delay layer comprises a nonwoven web having a basis weight in a range of about 0.5 osy (17 gsm) to about 1.0 osy (34 gsm) and comprising polyolefin fibers having a denier in a range of about 2.0 to about 3.0.

21. A personal care absorbent article comprising:

a fluid intake/distribution layer; and a fluid transfer delay layer disposed beneath said fluid intake/distribution layer, said fluid transfer delay layer enabling a transfer of fluid from the fluid intake/distribution layer to a pad layer disposed beneath said fluid transfer delay layer while still allowing fluid distribution by said fluid intake/distribution layer along a machine direction of the article resulting in saturation levels of less than about 0.86 g/g/in of fluid in said fluid intake/distribution layer obtained from a Flat System Testing Procedure;

said fluid transfer delay layer enabling a fluid intake time for said intake/distribution layer of less than about 39 seconds obtained from an Intake/Rewet Test and a rewet value for said fluid intake/distribution layer of less than about 0.88 g obtained from an Intake/Rewet Test;

wherein the fluid transfer delay layer has one of a permeability greater than about 530 darcies and a capillarity ($\Delta P/\gamma$) greater than or equal to about 0.0020 microns$^{-1}$.

* * * * *